(12) United States Patent
Rijken et al.

(10) Patent No.: US 11,410,307 B2
(45) Date of Patent: Aug. 9, 2022

(54) SECOND READER

(71) Applicant: Kheiron Medical Technologies Ltd, London (GB)

(72) Inventors: Tobias Rijken, London (GB); Michael O'Neill, London (GB); Andreas Heindl, London (GB); Joseph Elliot Yearsley, London (GB); Dimitrios Korkinof, London (GB); Galvin Khara, London (GB); Peter Kecskemethy, London (GB); Edith Karpati, Budapest (HU)

(73) Assignee: KHEIRON MEDICAL TECHNOLOGIES LTD, London (GB)

( * ) Notice: Subject to any disclaimer, the term of this patent is extended or adjusted under 35 U.S.C. 154(b) by 0 days.

(21) Appl. No.: 17/251,354

(22) PCT Filed: Jun. 14, 2019

(86) PCT No.: PCT/GB2019/051667
§ 371 (c)(1),
(2) Date: Dec. 11, 2020

(87) PCT Pub. No.: WO2019/239154
PCT Pub. Date: Dec. 19, 2019

(65) Prior Publication Data
US 2021/0248744 A1    Aug. 12, 2021

(30) Foreign Application Priority Data

Jun. 14, 2018  (GB) .................................... 1809796
Nov. 27, 2018  (GB) .................................... 1819329
Jan. 7, 2019   (GB) .................................... 1900212

(51) Int. Cl.
*G06T 7/00*     (2017.01)
*G16H 30/40*    (2018.01)
(Continued)

(52) U.S. Cl.
CPC ............ *G06T 7/0012* (2013.01); *A61B 6/502* (2013.01); *A61B 6/5205* (2013.01);
(Continued)

(58) Field of Classification Search
CPC . G06T 7/0012; G06T 7/11; G06T 7/70; G06T 2207/20076; G06T 2207/20081;
(Continued)

(56) References Cited

U.S. PATENT DOCUMENTS 5,768,406 A    6/1998  Abdel-Mottaleb
5,999,639 A    12/1999 Rogers et al.
(Continued)

FOREIGN PATENT DOCUMENTS

GB      2579244 A8     6/2020
JP    2013-039230 A    2/2013
(Continued)

OTHER PUBLICATIONS

UK Intellectual Property Office; Search Report for GB1819329.2 dated May 28, 2019.
(Continued)

*Primary Examiner* — Vu Le
*Assistant Examiner* — Winta Gebreslassie
(74) *Attorney, Agent, or Firm* — Finch & Maloney PLLC

(57) ABSTRACT

The present invention relates to a method and system that automatically determines malignancy in mammograms in parallel with a human operator. More particularly, the present invention relates to providing a reliable automated malignancy determination in parallel to a human operator to reduce the need for two human operators in a mammography analysis workflow.
Aspects and/or embodiments seek to provide a method of automatically assessing mammography data in parallel with a human operator. Aspects and/or embodiments also seek to
(Continued)

address the problems relating to providing a substantially reliable second reader to allow a single operator to analyse and diagnose mammography data.

19 Claims, 5 Drawing Sheets

(51) Int. Cl.

| | | |
|---|---|---|
| *A61B 6/00* | (2006.01) | |
| *G06K 9/46* | (2006.01) | |
| *G06N 3/08* | (2006.01) | |
| *G16H 40/67* | (2018.01) | |
| *G06K 9/62* | (2006.01) | |
| *G06T 7/11* | (2017.01) | |
| *G06T 7/70* | (2017.01) | |
| *G16H 30/20* | (2018.01) | |
| *G16H 50/20* | (2018.01) | |
| *G06T 7/143* | (2017.01) | |
| *G06V 10/764* | (2022.01) | |
| *G06V 10/774* | (2022.01) | |
| *G06V 30/19* | (2022.01) | |

(52) U.S. Cl.
CPC .......... *A61B 6/5217* (2013.01); *A61B 6/5235* (2013.01); *G06K 9/6256* (2013.01); *G06K 9/6267* (2013.01); *G06N 3/08* (2013.01); *G06T 7/11* (2017.01); *G06T 7/143* (2017.01); *G06T 7/70* (2017.01); *G06V 10/764* (2022.01); *G06V 10/774* (2022.01); *G06V 30/19147* (2022.01); *G06V 30/19173* (2022.01); *G16H 30/20* (2018.01); *G16H 30/40* (2018.01); *G16H 40/67* (2018.01); *G16H 50/20* (2018.01); *G06T 2207/10081* (2013.01); *G06T 2207/10088* (2013.01); *G06T 2207/10116* (2013.01); *G06T 2207/10132* (2013.01); *G06T 2207/20076* (2013.01); *G06T 2207/20081* (2013.01); *G06T 2207/20084* (2013.01); *G06T 2207/30068* (2013.01); *G06T 2207/30096* (2013.01); *G06V 2201/03* (2022.01)

(58) Field of Classification Search
CPC ... G06T 2207/2008; G06T 2207/30068; G06T 2207/30096; G06T 2207/20084; G06T 2207/10116; G16H 30/40; A61B 6/502; A61B 6/5205; A61B 6/5217; A61B 6/5235; G06K 9/6256; G06K 9/6267; G06K 2209/05; G06N 3/08; G06N 20/00
See application file for complete search history.

(56) References Cited

U.S. PATENT DOCUMENTS

| | | | |
|---|---|---|---|
| 6,058,322 | A | 5/2000 | Nishikawa et al. |
| 6,574,304 | B1 | 6/2003 | Hsieh et al. |
| 7,490,085 | B2 | 2/2009 | Walker et al. |
| 10,223,610 | B1* | 3/2019 | Akselrod-Ballin ............. G06K 9/6273 |
| 2004/0184644 | A1* | 9/2004 | Leichter ............. G06K 9/033 382/128 |
| 2004/0228509 | A1 | 11/2004 | Holupka et al. |
| 2005/0010445 | A1 | 1/2005 | Krishnan et al. |
| 2005/0049497 | A1 | 3/2005 | Krishnan |
| 2006/0100507 | A1 | 5/2006 | Mertelmeier |
| 2006/0122467 | A1 | 6/2006 | Harrington et al. |
| 2006/0177125 | A1 | 8/2006 | Chan et al. |
| 2007/0183641 | A1* | 8/2007 | Peters ............. G06T 7/0012 382/131 |
| 2008/0159613 | A1* | 7/2008 | Luo ............. G06T 7/0012 382/132 |
| 2009/0041327 | A1* | 2/2009 | Chen ............. G06T 7/0012 382/132 |
| 2009/0118640 | A1 | 5/2009 | Miller et al. |
| 2009/0274349 | A1 | 11/2009 | Cascio et al. |
| 2010/0135562 | A1 | 6/2010 | Greenberg et al. |
| 2010/0256459 | A1 | 10/2010 | Miyasa et al. |
| 2010/0256991 | A1 | 10/2010 | Ishikawa et al. |
| 2012/0099771 | A1 | 4/2012 | Lao |
| 2013/0218045 | A1 | 8/2013 | Ironstone |
| 2013/0236078 | A1 | 9/2013 | Kobayashi et al. |
| 2013/0322711 | A1 | 12/2013 | Schultz et al. |
| 2014/0018681 | A1 | 1/2014 | Chang et al. |
| 2016/0177125 | A1 | 6/2016 | Flosser et al. |
| 2016/0314579 | A1 | 10/2016 | Ghouti et al. |
| 2016/0361121 | A1 | 12/2016 | Reicher et al. |
| 2016/0364528 | A1 | 12/2016 | Reicher et al. |
| 2016/0364857 | A1 | 12/2016 | Reicher et al. |
| 2017/0200266 | A1 | 7/2017 | Podilchuk et al. |
| 2018/0033144 | A1 | 2/2018 | Risman et al. |
| 2019/0189263 | A1 | 6/2019 | Stoval, III et al. |
| 2019/0340763 | A1 | 11/2019 | Laserson |
| 2021/0035296 | A1 | 2/2021 | Mahrooghy et al. |
| 2021/0312618 | A1 | 10/2021 | Kecskemethy et al. |
| 2021/0313043 | A1 | 10/2021 | Kecskemethy et al. |

FOREIGN PATENT DOCUMENTS

| | | |
|---|---|---|
| WO | 99/05503 A3 | 4/1999 |
| WO | 2005/001740 A2 | 1/2005 |
| WO | 2005/001742 A2 | 1/2005 |
| WO | 2016/057960 A1 | 4/2016 |

OTHER PUBLICATIONS

Intl Search Report, PCT/GB2019/051668, dated Nov. 1, 2019.
Intl Search Report, PCT/GB2019/051666, dated Nov. 6, 2019.
Intl Search Report, PCT/GB2019/051666, dated Sep. 23, 2019.
UK Intellectual Property Office; Search Report for GB1809796.4 dated Dec. 17, 2018.
Z Huo et al, "Computerized analysis of multiple-mammographic views: potential usefulness of special view mammograms in computer-aided diagnosis", IEEE Trans Med Imaging Dec. 2001; 20(12):1285-92, DOI: 10.1109/42.974923 (Abstract).
Written Opinion of the International Searching Authority, PCT/GB2019/051667.
IPRP, PCT/GB2019/051667, dated May 10, 2020.
Written Opinion of the International Searching Authority, PCT/GB2019/051668.
IPRP, PCT/GB2019/051668, dated May 10, 2020.
Written Opinion of the International Searching Authority, PCT/GB2019/051666.
IPRP, PCT/GB2019/051666, dated May 10, 2020.
Canadian Patent Application 3,102,170, PCT/GB2019/051666; Requisition by Examiner dated Jul. 27, 2021.
K. He, G. Gkioxari, P. Dollár and R. Girshiok, "Mask R-CNN," 2017 IEEE International Conference on Computer Vision (ICCV), 2017, pp. 2980-2988, doi: 10.1109/ICCV.2017.322.
Paul F. Jaeger et al "Retina U-Net: Embarrassingly Simple Exploitation of Segmentation Supervision for Medical Object Detection" (https://arxiv.org/pdf/1811.08661.pdf).
EP Patent Appln 19744778.2, "Communication Under Rule 71 (3) EPC", Intention to Grant dated Sep. 7, 2021.
EP Patent Appln 19744779.0, "Communication Under Rule 71 (3) EPC", Intention to Grant dated Sep. 29, 2021.
EP Patent Appln 19744777.4, "Communication Under Rule 71 (3) EPC", Intention to Grant, dated Sep. 30, 2021.
Canadian Intellectual Property Office; Examiner's Requisition for Application No. 3,102,173 (PCT No. GB2019051667) dated Jun. 29, 2021.
Canadian Intellectual Property Office; Examiner's Requisition for Application No. 3, 102, 174 (PCT No. GB2019051668) dated Jul. 6, 2021.

(56) References Cited

OTHER PUBLICATIONS

U.S. Appl. No. 17/251,398, office action dated Sep. 1, 2021.
Dezso Ribli et al. "Detecting and classifying lesions in mammograms with Deep Learning", Sci Rep 2018: 8: 4165, published online Mar. 15, 2018. Doi: 10.1038/s41598-018-22437-z.
Zhimin Huo et al, "Computerized analysis of multiple-mammographic views: potential usefulness of special view mammograms in computer-aided diagnosis", IEEE Trans Med Imaging Dec. 2001; 20(12):1285-92, DOI: 10.1109/42.974923 (Abstract).
Yufeng Zheng et al. "Breast Cancer Screening Using Convolutional Neural Network and Follow-up Digital Mammography", Proceedings of spie, vol. 10669, May 14, 2018 (May 4, 2018), pp. 1066905-1066905, XP060105634, DOI: 10.1117/122304564.
Kisilev Pavel et al., "Medical Image Description Using Multi-task loss CNN", Sep. 27, 2016, Intelligent Virtual Agent.IVA 2015. LNCS: [Lecture Notes in Computer Science; Lect. Notes in Comuter], Springer, Berlin, Heidelberg, pp. 121-129, XP047410045, ISBN: 978-3-642-17318-9.
WOSA, PCT/GB2019/051667.
IPRP, PCT/GB2019/051667, dated Oct. 5, 2020
Canadian Intellectual Property Office; Examiner's Requisition for Application No. 3,102,173, (PCT No. GB20190516670 dated Dec. 9, 2021. 6 pages.
Canadian Patent Application 3,102,170, PCT/GB2019/051666; Requisition by Examiner, dated Jan. 11, 2022. 5 pages.
He, "A Review on Automatic Mammographic Density and Parenchymal Segmentation," International Journal of Breast Cancer, vol. 2015, Article ID 276217, (2015) 31 pages.

\* cited by examiner

SECOND READER

CROSS REFERENCE TO RELATED APPLICATIONS

This application is a national stage patent application filed under 35 U.S.C. § 371 of PCT International patent application PCT/GB2019/051667, filed Jun. 14, 2019, and claiming priority to GB patent application 1809796.4, filed Jun. 14, 2018, GB patent application 1819329.2, filed Nov. 27, 2018 and GB patent application 1900212.0 filed Jan. 7, 2019, the entire contents of each of which are incorporate by reference.

FIELD

The present invention relates to a method and system that substantially automatically determines malignancy in mammograms in parallel with a human operator. More particularly, the present invention relates to providing a reliable automated malignancy determination in parallel to a human operator to reduce the need for two human operators in a mammography analysis workflow.

BACKGROUND

Mammography is a medical imaging modality widely used for breast cancer detection. Mammography makes use of "soft" X-rays to produce detailed images of the internal structure of the human breast. These images are called mammograms and use of mammography is considered to be the gold standard in the early detection of breast abnormalities (which can provide a valid diagnosis of a cancer in a curable phase).

Unfortunately, the procedure of analysing mammograms is often challenging. The density and tissue type of the breasts are highly varied and in turn present a high variety of visual features due to patient genetics. These background visual patterns can obscure the often-tiny signs of malignancies which may then be easily overlooked by the human eye. Thus, the analyses of mammograms often lead to false-positive or false-negative diagnostic results which may cause missed treatment (in the case of false-negatives) as well as unwanted psychological and sub-optimal downstream diagnostic and treatment consequences (in the case of false-positives).

Most developed countries maintain a population-wide screening program, i.e. a comprehensive system for calling in women of a certain age group, free of symptoms, to have regular breast screening. These screening programs require highly standardised protocols to be followed by trained and experienced specialist doctors who can reliably analyse a large number of mammograms routinely. Most professional guidelines strongly suggest the reading of each mammogram by two equally expert radiologists (an approach known as double-reading). Nowadays, with the number of available highly skilled radiologists being scarce, and decreasing, the double-reading approach is often impractical or impossible.

The involvement of two expert radiologists significantly increases the cost of each case and also prolongs the time for a patient to receive the results of a scan. In some cases, a suspicious lesion may even be missed by both expert radiologists.

Therefore, there is a need to improve, if not at least maintain, the quality of mammography results whilst adhering to guidelines that require or strongly suggest a double-read process.

SUMMARY OF THE INVENTION

Aspects and/or embodiments seek to provide a method of substantially automatically assessing mammography data in parallel with a human operator. Aspects and/or embodiments also seek to address the problems relating to providing a substantially reliable second reader to allow a single operator to analyse and diagnose mammography data.

According to a first aspect, there is provided a computer-aided method of analysing mammographic images, the method comprising the steps of receiving a plurality of mammograms (10); performing a first analysis (30) on the plurality of mammograms (10) comprising identifying a malignancy classification for each of the mammograms; determining a malignancy output value (30Y) for each of mammograms dependent upon the first analysis (30); determining an average malignancy output value by averaging the malignancy output values for the plurality of mammograms; thresholding the average malignancy output value to generate an output binary malignancy value (60Y); performing a second analysis (40) on the plurality of mammograms (30X) to determine a plurality of localisation data parameters (40X) for each mammogram; and generating (70) output localisation data for the plurality of mammograms in dependence upon the output binary malignancy value.

In this way, the need for an additional highly skilled medical professional to perform a second reading of the mammogram can be eliminated and the second read can be performed automatically, and substantially instantaneously. The method may also reduce the risk of human error.

By receiving multiple input images, radiologists can perform case-wise analysis for patients and substantially determine the likelihood of a malignant lesion after analysing multiple mammographic views. In order to combat the generation of multiple false-positives that can limit the effectiveness/reliability of current machine learning based methods, the method may only provide localisation data for lesions if the analysis from the case-wise review of the mammograms suggest there is a malignant lesion.

Optionally, there can be performed the further step of pre-processing a plurality of mammograms to improve malignancy classification for each of the mammograms, the step of pre-processing further comprising the use of one or more trained neural networks. Primarily, convolutional neural networks can be used but other types may be used, such as capsule networks.

Optionally, the step of performing the first analysis on the plurality of mammograms is conducted using one or more trained convolutional neural network classifier. As an example, the convolutional neural networks (or CNNs) can be ConvNets.

Optionally, the weights of the trained convolutional neural network classifier are frozen in dependence upon data used to train the convolutional neural network classifier.

Optionally, the plurality of mammograms comprises: a left side cranial caudal mammogram, L-CC; a right side cranial caudal mammogram, R-CC; a left side medio-lateral-oblique mammogram, L-MLO; and a right side medio-lateral-oblique mammogram, R-MLO.

Optionally, the average malignancy output value comprises any combination of; an average value for all L-CC malignancy output values; an average value for all R-CC malignancy output values; an average value for all L-MLO malignancy output values; an average value for all R-MLO malignancy output values; an average value for all left-side mammogram malignancy output values; and an average value for all right-side mammogram malignancy output values.

Optionally, a max operator is performed between the average value for all left-side mammogram malignancy output values and the average value for all right-side mammogram malignancy output values to determine the average malignancy output value.

Optionally, the step of performing a second analysis on the plurality of mammograms is conducted using one or more trained regional convolutional neural network, RCNN.

Optionally, the one or more trained RCNNs comprises a plurality of sub-divisional networks to determine the plurality of localisation data parameters, the sub-divisional networks provide any one or combination of: a bounding box generation model; a segmentation model; and a malignancy classification type model.

Optionally, the one or more RCNNs are coupled to an output convolutional layer of the one or more convolutional neural network used to perform the first analysis. Optionally, the one or more RCNNs are trained using the weights of the of the one or more convolutional neural network used to perform the first analysis.

Optionally, the one or more trained RCNNs generates an overlay mask indicating a lesion of interest, the mask further comprises a malignancy probability value.

Optionally, the bounding box generation model generates bounding box regression with none-max suppression in order to locate lesions of interest.

Optionally, the segmentation model provides a segmentation outlines of anatomical regions and/or lesions, the segmentation model further comprises localisational characteristics.

Optionally, the malignancy classification type model identifies a tissue type and density category classification for the breast.

Optionally, the sub-divisional networks comprise an ensemble of masks created by the sub-division networks. Optionally, the one or more RCNNs are ensembled with non-max suppression and/or weighted box clustering.

Optionally, the step of thresholding the average malignancy output values comprises selecting multiple operating points of the mammogram, optionally, selecting at least six operating points.

According to a second aspect, there is provided a method of training one or more convolutional neural networks to perform the steps of any preceding claim, the method comprising: receiving one or more mammograms; training one or more convolutional neural networks to wholly analyse the one or more mammograms and determining a malignancy value; freeze the weights for the one or more convolutional neural networks; add RCNNs to the last convolutional layer of the one or more convolutional neural network; and train the RCNNs using the frozen weights of the one or more convolutional neural networks.

Optionally, the RCNNs comprise mask-RCNN heads.

Optionally, the one or more mammograms are restricted to 4000×4000 pixels.

Optionally, the mammograms are pre-processed using any one or a combination of: windowing; resampling; and normalization.

According to a third aspect, there is provided an apparatus operable to perform the method of any preceding feature.

According to a fourth aspect, there is provided a system operable to perform the method of any preceding feature.

According to a fifth aspect, there is provided a computer program product operable to perform the method of any preceding feature.

BRIEF DESCRIPTION OF DRAWINGS

Embodiments will now be described, by way of example only and with reference to the accompanying drawings having like-reference numerals, in which.

SPECIFIC DESCRIPTION

Figure 1:
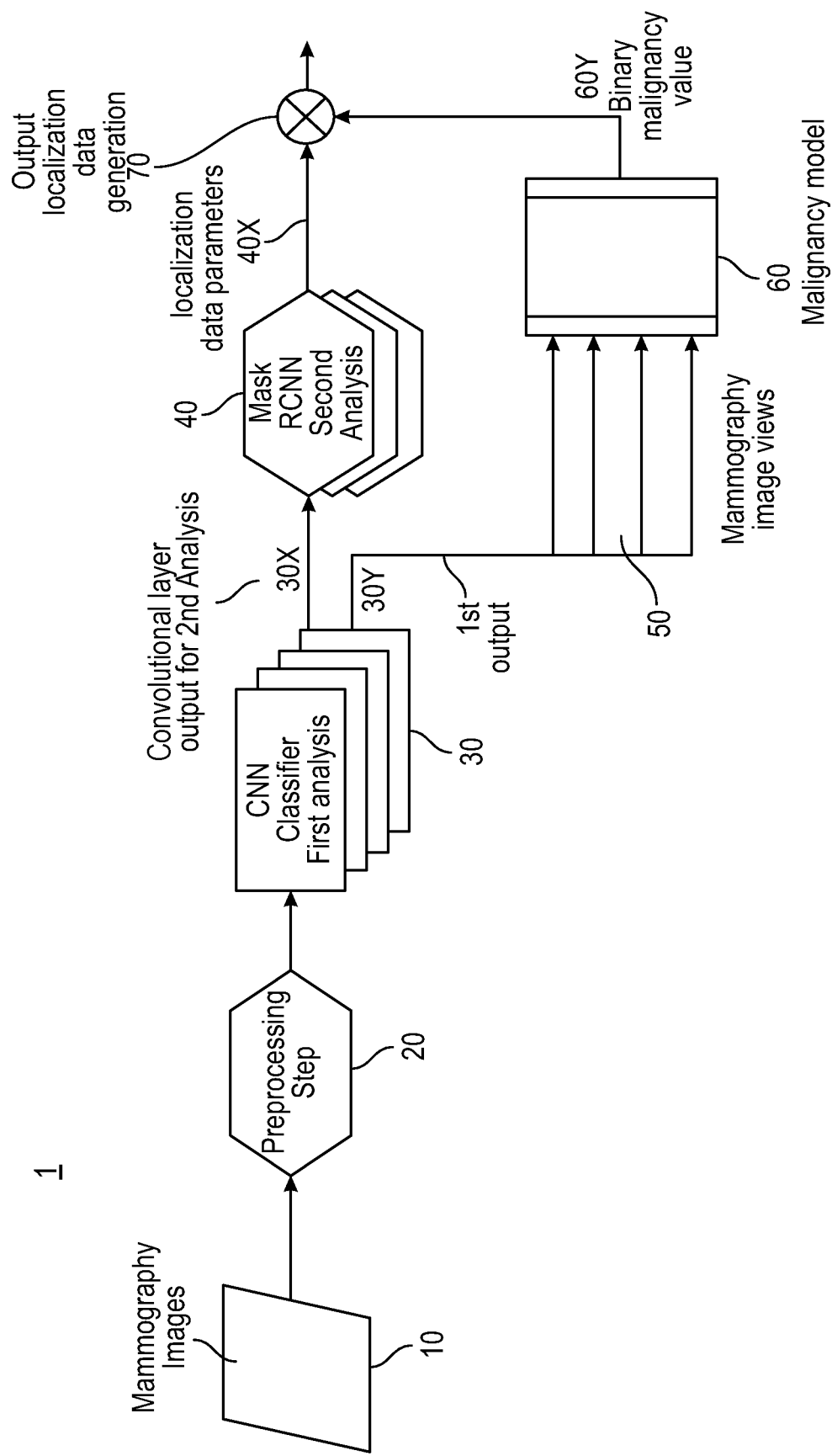
FIG. 1 illustrates a flowchart showing an outline of the method of an embodiment.
Figure 2:
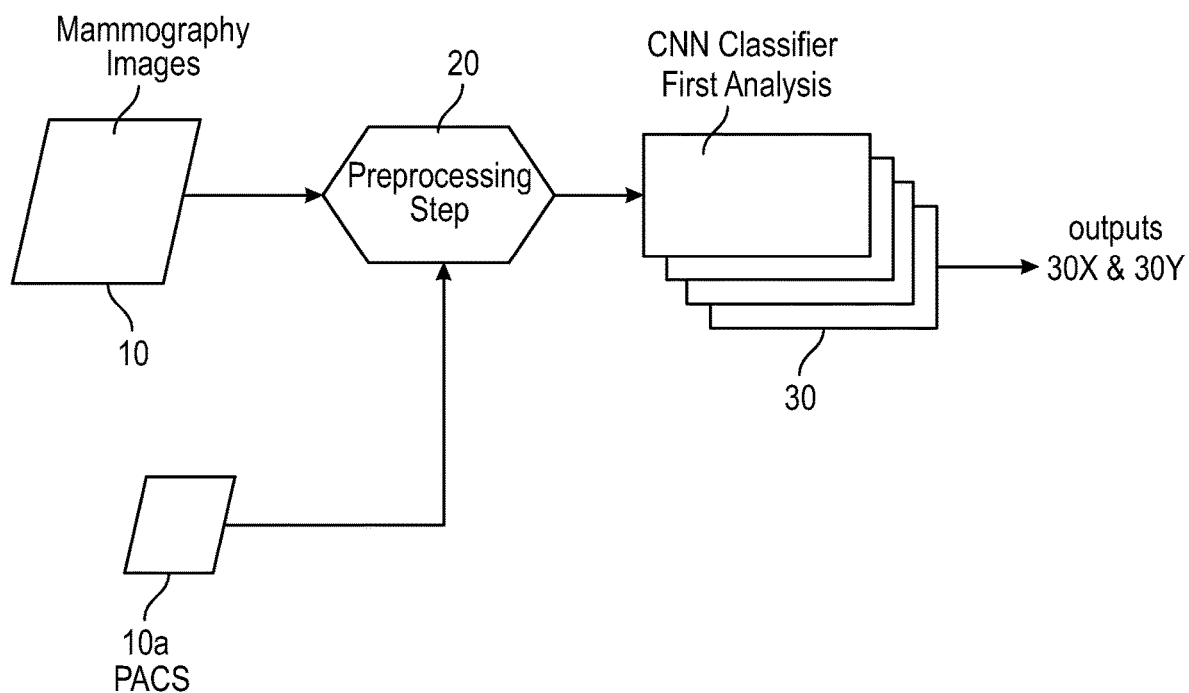
FIG. 2 illustrates the portion of the flowchart of FIG. 1 focused on providing a malignancy output based on the input image and the pre-trained malignancy detection neural network, optionally showing the pre-processing that can be applied to the input image.

FIG. 1 depicts an example embodiment which will now be described in more detail below with reference to FIGS. 2 to 5 as appropriate.

Referring first to FIG. 1, there is shown a method for receiving input mammography images 10 and outputting a malignancy output, for example a yes/no binary output or a more detailed output showing regions of interest along with a binary output.

In a medical scan of a patient (mammography), the scanned images are collated in DICOM format, which is a file format commonly used to store medical images. The method uses pre-processed data that is stored on a Picture Archiving Communication Systems (PACS) (FIG. 2, 10a) that radiology departments use in hospitals. The output of this method also enriches the PACS database to improve future applications of analysing mammographic images.

In some instances, the images can be pre-processed 20 using a variety of methods, including but not restricted to, windowing, resampling and normalisation. The input images may also undergo domain adaption and/or style transfer techniques to further improve the results.

The mammograms, pre-processed or not, are then fed into a convolutional neural network (CNN) classifier 30 which has been trained to analyse the images and assess whether the image shows a malignant lesion. In some embodiments, there is use of more than one trained CNN to complete this task. Conventional methods of detected malignant lesions in a mammogram may also be used.

In order for a CNN to operate as a malignancy model the network first needs to be trained. Similar to the pre-processing methods mentioned above, input images for the purpose of training the network may undergo windowing, resampling, normalisation, etc., before the images are used. In some instances, the images used to train the network are either provided or sized to up to 4000×4000 pixels.

As the images are fed through the CNN, a number of stacked mathematical operations are performed. In doing so, the CNN applies variable tensors to the previous layer such that a malignant or not score is produced as a result of these operations. We then update the variables based on the gradient of the cost function (cross-entropy) making use of the chain-rule to work out the gradient updates to apply. In this way, multiple CNNs can be trained to be used with the described aspects/embodiments.

Additionally, the training of the CNNs may include concatenating a previous image taken of the same mammographic view and run it through the networks together with the current image being fed into the network. This enables the fine tuning of the final few layers of the CNN such that they can account for multiple images.

Figure 3:
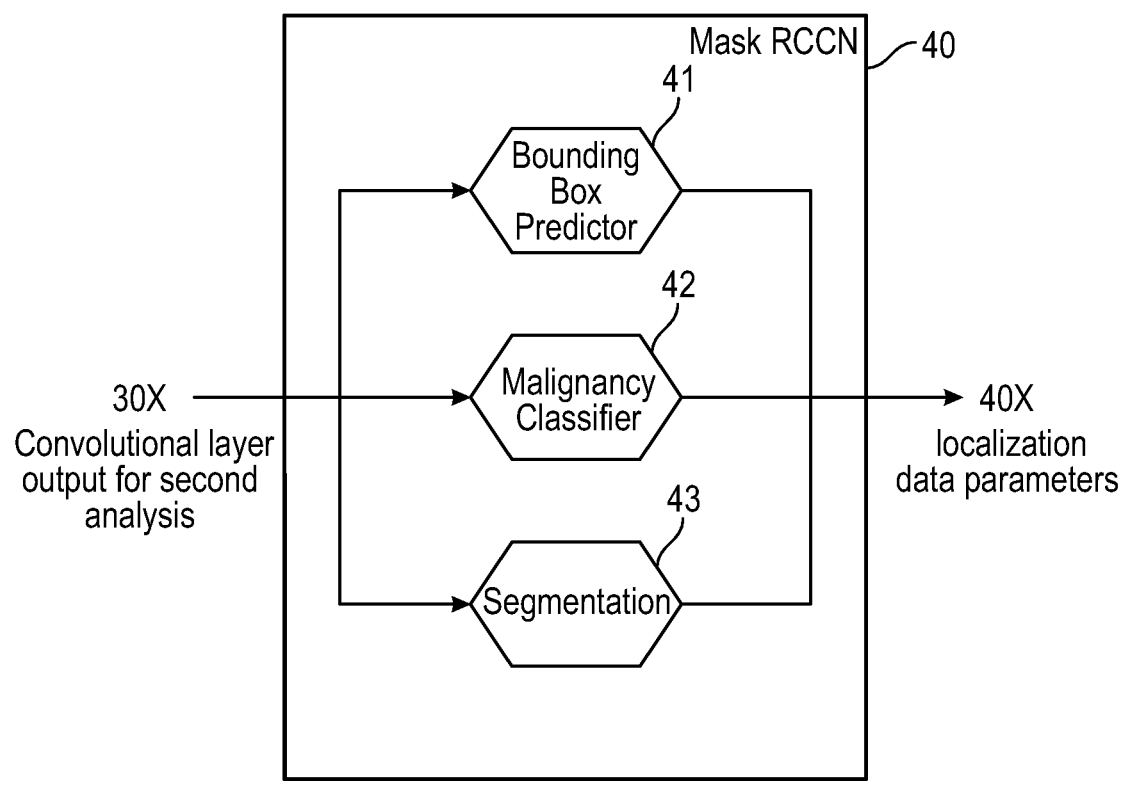
FIG. 3 illustrates the Mask-RCNN of the embodiment of FIG. 1 in more detail.

Once the malignancy model(s) are trained, the network and its weights are frozen. We then take one of the convolutional layer's outputs (30X) which is then feed into mask heads from a Mask RCNN 40. An exemplary Mask RCNN is illustrated in FIG. 3. These heads include a bounding box predictor 41, where the bounding boxes can be used to cut out a part of the original image. In addition to, or on top of the cut-out patch, a malignant classifier 42 and segmentation 43 heads are placed. As with the malignancy model, any conventional bounding box, malignancy classifier or segmentation models can be used with this system. In "Mask R-CNN," 2017 IEEE International Conference on Computer Vision (ICCV), 2017, pp. 2980-2988, doi: 10.1109/ICCV.2017.322, Kaiming He, et al. describes a traditional RCNN that can be used in at least some embodiments, which is incorporated by reference.

There are various methods of training the RCNNs. Firstly, connecting the malignancy model to the Mask RCNN the Mask RCNN heads can be trained at the same time as the whole image malignancy model. Secondly, it is also possible to train the Mask RCNN without freezing the malignancy model network. Finally, the Mask RCNN heads may be trained with multiple malignancy models. Thus, the method of training the Mask RCNN heads is not restricted to a certain type, which enables the approach to be tailored for specific uses.

Once the neural networks are trained, during use, or at inference time, the malignancy model is frozen based on the training data.

Figure 4:
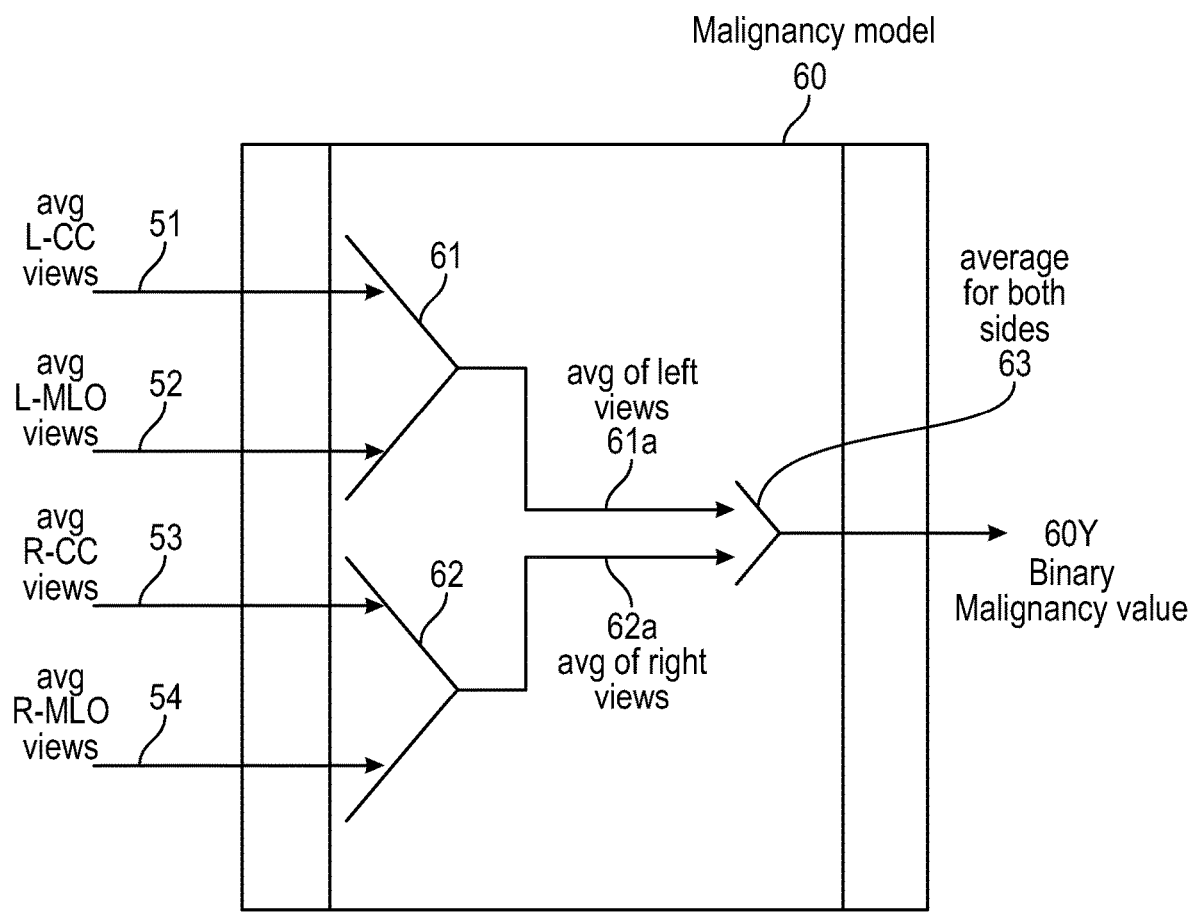
FIG. 4 illustrates the portion of the flowchart of FIG. 1 showing the process of the mean and max operations performed by the embodiment.

A second output 30Y from the CNN classifier may be a set of predetermined images 50. As an example, during run time, the system of the embodiment receives four types of mammography images 50: left cranial caudal view (L-CC) 51, right cranial caudal view (R-CC) 53, left medio-lateral-oblique (L-MLO) 52 and a right medio-lateral-oblique (R-MLO) 54 (FIG. 4). This combination of images is known to be referred to as a case. Upon passing though the malignancy model or models (60), the system of the embodiment produces an entire case of outputs. These outputs are then averaged to generate a single output 60Y.

As seen in FIG. 4, 51 represents an average score of all left cranial caudal views, 52 represents an average score of all left medio-lateral-oblique (L-MLO) views, 53 represents an average score of all right cranial caudal (R-CC) views and 54 represents an average score of all right medio-lateral-oblique (R-MLO) views. As depicted by 61*a* and 62*a*, the system of the embodiment then calculates a mean of the respective left side views 61 and right side views 62. This results in a malignancy output for each side. A max operation 63 is then performed for the average malignancy outputs for each side.

Although not depicted in the figures, in the described embodiment the method then thresholds this result with a predetermined threshold which gives a binary malignant or not score 60Y.

Figure 5:
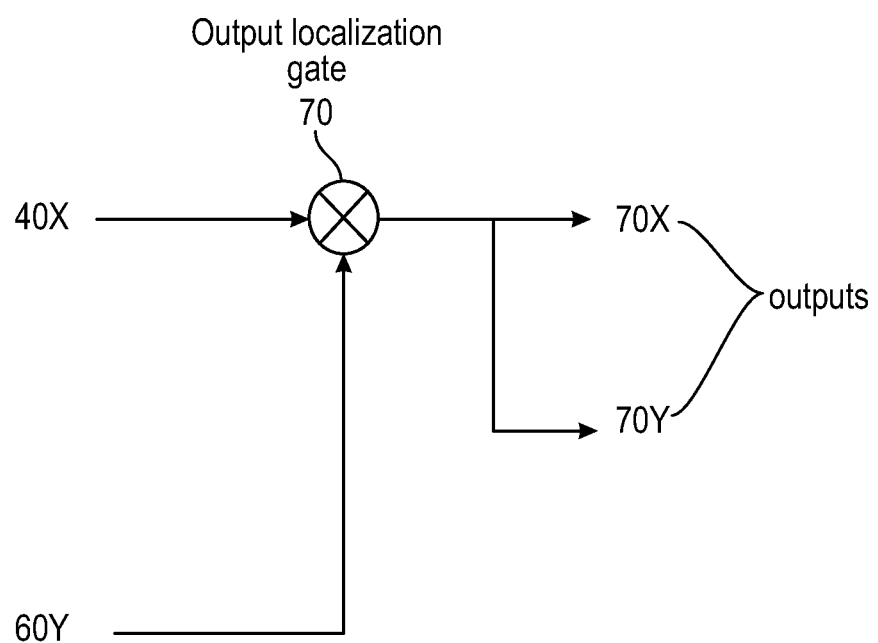
FIG. 5 illustrates how the final output of the embodiment of FIG. 1 is determined.

Finally, with reference to FIG. 5, the output binary malignancy value 60Y is used to gate whether or not to show the Mask RCNN segmentations or bounding boxes 40X. In this way, instead of showing absolutely all lesions detected by the Mask RCNN alone, which leads to numerous false-positives, the resulting Mask R-CNN outputs (e.g., 70X and 70Y are only shown if the binary malignant score is positive, i.e., indicating malignancy. When 60Y does not indicate the case to be malignant, the Mask RCNN outputs are ignored and no localisation data is produced as an output of the system.

In some cases, the Mask RCNN results can be ensembled by interpolating between bounding box coordinates (of shape [N, M, x1, x2, y1, y2] where N represents the number of models and M the maximum number of bounding boxes) which have a sufficient intersection over union (IOU), which is predetermined. Any bounding box which does not have a sufficient IOU with the others are removed from consideration. With the resulting bounding boxes, the raw segmentation masks are then averaged before thresholding with a predetermined threshold, and also averaging the lesion scores for all of the sufficient bounding boxes.

These operations result in a final set of bounding boxes of shape [1, M, x1, x2, y1, y2] along with a segmentation mask of shape [1, H, W] and lesion scores of shape [1, M]. A better way is to use weighted box clustering (WBC) which is described by Paul F. Jaeger et al in "Retina U-Net: Embarrassingly Simple Exploitation of Segmentation Supervision for Medical Object Detection" (https://arxiv.org/pdf/1811.08661.pdf), which is incorporated by reference.

As aforementioned, double reading is the gold standard in breast cancer screening with mammography. In this scenario, two radiologists will report on a case. Arbitration will occur when the two readers are not in agreement about whether to recall a patient for further screening tests.

In the present embodiment, the described system is able to operate as an independent second reader. In the past, computer aided diagnosis systems were not able to act as such due to a high false positive rate. Similar to a human radiologist, the described system of the embodiment can have a low false positive rate which means it can be used in at least the following two ways:
 1. As a truly independent second reader: a first (human) radiologist looks at the case and the present system independently assesses the case. If the two disagree, the system of the embodiment shows the outlines for lesions of interest for the human radiologist to consider, and if they agree, the radiologist does not see the outputs of the system; or
 2. As a non-independent second reader where the human radiologist and the system of the embodiment both analyse the case—in that the human radiologist is supported by the system of the embodiment. The radiologist can click to see the results generated by the system of the embodiment whenever they want.

Many approaches that mimic the techniques used by human radiologists can be incorporated in the system in some embodiments, such as using a previous image as a reference to look for any changes since the last scan and also a mean then max operator to mimic the way human radiologists trade off calling back a case.

Machine learning is the field of study where a computer or computers learn to perform classes of tasks using the feedback generated from the experience or data gathered that the machine learning process acquires during computer performance of those tasks.

Typically, machine learning can be broadly classed as supervised and unsupervised approaches, although there are particular approaches such as reinforcement learning and semi-supervised learning which have special rules, techniques and/or approaches. Supervised machine learning is concerned with a computer learning one or more rules or functions to map between example inputs and desired outputs as predetermined by an operator or programmer, usually where a data set containing the inputs is labelled.

Unsupervised learning is concerned with determining a structure for input data, for example when performing pattern recognition, and typically uses unlabelled data sets. Reinforcement learning is concerned with enabling a computer or computers to interact with a dynamic environment, for example when playing a game or driving a vehicle.

Various hybrids of these categories are possible, such as "semi-supervised" machine learning where a training data set has only been partially labelled. For unsupervised machine learning, there is a range of possible applications such as, for example, the application of computer vision techniques to image processing or video enhancement. Unsupervised machine learning is typically applied to solve problems where an unknown data structure might be present in the data. As the data is unlabelled, the machine learning process is required to operate to identify implicit relationships between the data for example by deriving a clustering metric based on internally derived information. For example, an unsupervised learning technique can be used to reduce the dimensionality of a data set and attempt to identify and model relationships between clusters in the data set, and can for example generate measures of cluster membership or identify hubs or nodes in or between clusters (for example using a technique referred to as weighted correlation network analysis, which can be applied to high-dimensional data sets, or using k-means clustering to cluster data by a measure of the Euclidean distance between each datum).

Semi-supervised learning is typically applied to solve problems where there is a partially labelled data set, for example where only a subset of the data is labelled. Semi-supervised machine learning makes use of externally provided labels and objective functions as well as any implicit data relationships. When initially configuring a machine learning system, particularly when using a supervised machine learning approach, the machine learning algorithm can be provided with some training data or a set of training examples, in which each example is typically a pair of an input signal/vector and a desired output value, label (or classification) or signal. The machine learning algorithm analyses the training data and produces a generalised function that can be used with unseen data sets to produce desired output values or signals for the unseen input vectors/signals. The user needs to decide what type of data is to be used as the training data, and to prepare a representative real-world set of data. The user must however take care to ensure that the training data contains enough information to accurately predict desired output values without providing too many features (which can result in too many dimensions being considered by the machine learning process during training, and could also mean that the machine learning process does not converge to good solutions for all or specific examples). The user must also determine the desired structure of the learned or generalised function, for example whether to use support vector machines or decision trees.

The use of unsupervised or semi-supervised machine learning approaches are sometimes used when labelled data is not readily available, or where the system generates new labelled data from unknown data given some initial seed labels.

Machine learning may be performed through the use of one or more of: a non-linear hierarchical algorithm; neural network; convolutional neural network; recurrent neural network; long short-term memory network; multi-dimensional convolutional network; a memory network; fully convolutional network or a gated recurrent network allows a flexible approach when generating the predicted block of visual data. The use of an algorithm with a memory unit such as a long short-term memory network (LSTM), a memory network or a gated recurrent network can keep the state of the predicted blocks from motion compensation processes performed on the same original input frame. The use of these networks can improve computational efficiency and also improve temporal consistency in the motion compensation process across a number of frames, as the algorithm maintains some sort of state or memory of the changes in motion. This can additionally result in a reduction of error rates.

Developing a machine learning system typically consists of two stages: (1) training and (2) production. During the training the parameters of the machine learning model are iteratively changed to optimise a particular learning objective, known as the objective function or the loss. Once the model is trained, it can be used in production, where the model takes in an input and produces an output using the trained parameters.

Any system feature as described herein may also be provided as a method feature, and vice versa. As used herein, means plus function features may be expressed alternatively in terms of their corresponding structure.

Any feature in one aspect may be applied to other aspects, in any appropriate combination. In particular, method aspects may be applied to system aspects, and vice versa. Furthermore, any, some and/or all features in one aspect can be applied to any, some and/or all features in any other aspect, in any appropriate combination.

It should also be appreciated that particular combinations of the various features described and defined in any aspects can be implemented and/or supplied and/or used independently.

The invention claimed is:

1. A computer-aided method of analysing mammographic images, comprising the steps of:
   receiving a plurality of mammograms;
   performing a first analysis on the plurality of mammograms comprising identifying a malignancy classification for each of the mammograms using a convolutional neural network (CNN) classifier;
   determining a malignancy output value for each of mammograms dependent upon the first analysis;
   determining an average malignancy output value by averaging the malignancy output values for the plurality of mammograms;
   thresholding the average malignancy output value to generate an output binary malignancy value;
   performing a second analysis using a mask regional convolutional neural network (mask R-CNN) on the plurality of mammograms to determine a plurality of localisation data parameters for each mammogram; and
   generating output localisation data for the plurality of mammograms in dependence upon the output binary malignancy value, wherein the second analysis comprises:
   generating a set of bounding boxes, wherein generating the set of bounding boxes comprises removing any bounding boxes not having a predetermined threshold of intersection over union and interpolating between bounding box coordinates;

generating averaged lesion scores, wherein generating the averaged lesion scores comprises averaging the lesion scores for the set of bounding boxes;

generating an averaged segmentation mask, wherein the averaged segmentation mask is generated by averaging a plurality of raw segmentation masks, before thresholding with a predetermined segmentation threshold; and wherein the output binary malignancy value is used to gate the output of the mask RCNN segmentations thereby minimizing mask RCNN false positives, such that the resulting mask RCNN segmentations are only output if the binary malignancy value is positive.

2. The method of claim 1 further comprising the step of pre-processing to plurality of mammograms to improve malignancy classification for each of the mammograms, the step of pre-processing further comprising the use of one or more trained neural networks.

3. The method of claim 1 wherein, the step of performing the first analysis on the plurality of mammograms is conducted using one or more trained convolutional neural network classifiers.

4. The method of claim 3 wherein the weights of the trained convolutional neural network classifier are frozen in dependence upon data used to train the convolutional neural network classifier.

5. The method of claim 1 wherein, the plurality of mammograms used to average the malignancy output values for the plurality of mammograms comprises:
a left side cranial caudal mammogram, L-CC;
a right side cranial caudal mammogram, R-CC;
a left side medio-lateral-oblique mammogram, L-MLO; and
a right side medio-lateral-oblique mammogram, R-MLO.

6. The method of claim 5 wherein, the average malignancy output value comprises any combination of:
an average value for all L-CC malignancy output values;
an average value for all R-CC malignancy output values;
an average value for all L-MLO malignancy output values;
an average value for all R-MLO malignancy output values;
an average value for all left-side mammogram malignancy output values; and
an average value for all right-side mammogram malignancy output values.

7. The method of claim 6, wherein a max operator is performed between the average value for all left-side mammogram malignancy output values and the average value for all right-side mammogram malignancy output values to determine the average malignancy output value.

8. The method of claim 1, wherein the RCNN is a trained RCNN and comprises a plurality of sub-divisional networks to determine the plurality of localisation data parameters, the sub-divisional networks provide any one or combination of:
a bounding box generation model;
a segmentation model; and
a malignancy classification type model.

9. The method of claim 8 wherein the RCNN is coupled to an output convolutional layer of the one or more convolutional neural network used to perform the first analysis.

10. The method of claim 9 wherein the RCNN is trained using the weights of the one or more convolutional neural network used to perform the first analysis.

11. The method of claim 8 wherein the RCNN generates an overlay mask indicating a lesion of interest, the mask further comprises a malignancy probability value.

12. The method of claim 8 wherein the bounding box generation model generates bounding box regression with none-max suppression in order to locate lesions of interest.

13. The method of claim 8 wherein the segmentation model provides a segmentation outlines of anatomical regions and/or lesions, the segmentation model further comprises localisational characteristics.

14. The method of claim 8 wherein the malignancy classification type model identifies a tissue type and density category classification for the breast.

15. The method of claim 8 wherein the sub-divisional networks comprise an ensemble of masks created by the sub-division networks.

16. The method of claim 15 wherein RCNN is ensembled with non-max suppression and/or weighted box clustering.

17. The method of claim 1 wherein the step of thresholding the average malignancy output values comprises selecting multiple operating points of the mammogram, optionally, selecting at least six operating points.

18. A method of training one or more convolutional neural networks to perform the steps according to claim 1, the method comprising:
receiving one or more mammograms;
training one or more convolutional neural networks to wholly analyse the one or more mammograms and determining a malignancy value;
freeze the weights for the one or more convolutional neural networks;
add RCNNs to the last convolutional layer of the one or more convolutional neural network;
and train the RCNNs using the frozen weights of the one or more convolutional neural networks.

19. The method of claim 18 wherein the mammograms are pre-processed using any one or a combination of: windowing; resampling; and normalization.

* * * * *